(12) United States Patent
Castagnino

(10) Patent No.: US 6,309,381 B1
(45) Date of Patent: Oct. 30, 2001

(54) USE OF HUMAN GROWTH HORMONE TO TREAT ACUTE MYOCARDIAL INFARCTION

(76) Inventor: Hugo E. Castagnino, Viamonte 752, 4th Fl., #7, Buenos Aires (AR)

( * ) Notice: Subject to any disclaimer, the term of this patent is extended or adjusted under 35 U.S.C. 154(b) by 0 days.

(21) Appl. No.: 09/144,715

(22) Filed: Sep. 1, 1998

(51) Int. Cl.⁷ .................................................. A61M 31/00
(52) U.S. Cl. ............................. 604/522; 514/12; 128/898
(58) Field of Search ............................... 128/898; 514/12, 514/810–811, 21; 530/399, 397, 362, 363; 604/500, 522

(56) References Cited

U.S. PATENT DOCUMENTS 5,140,008 * 8/1992 Jorgensen .............................. 514/12
5,849,704 * 12/1998 Sorensen ............................... 514/12

OTHER PUBLICATIONS

Castagnino et al. "Preservation of the Myocardial Collagen Framework by Human Growth–Hormone in Experimental Infarctions and reduction in the Incidence of Ventricular Aneurysms", 1992 (Abstract Only) Intnl J Card, 35(1): pp. 101–114.*

Novo Nordisk fact sheet for human growth hormone: 8/2000 HTTP://health.novo.dk/health/hgh/facts.asp.*

* cited by examiner

*Primary Examiner*—David J. Isabella
*Assistant Examiner*—Kelly O'Hara
(74) *Attorney, Agent, or Firm*—William B. Ritchie

(57) ABSTRACT

A method of treating an acute myocardial infarction (AMI) using human growth hormone to prevent most of the complications and the destructive process of cells and collagen framework which are linked to the AMI. This treatment can be used alone or in combination with other well-known methods of treatment.

5 Claims, No Drawings

USE OF HUMAN GROWTH HORMONE TO TREAT ACUTE MYOCARDIAL INFARCTION

BACKGROUND OF THE INVENTION

1. Field of the Invention

The invention relates to methods of treatment of acute myocardial infarction (AMI), in particular, treatment of AMI close to the onset in order to avoid most of the complications and the destructive race of cells and collagen framework which are linked to the AMI.

2. Description of the Related Art

For about thirty years, human growth hormone has been proposed as a possible treatment for various diseases and medical problems, such as to stimulate the fibroblasts; also to include neoangiogenesis. Efforts to reach profound degrees of experimental hibernation in animals only became possible when the threshold of ventricular fibrillation was raised through the use of human growth hormone.

More recently, other investigations with human growth hormone and isolated growth factors, (like IGF1; FGF and TGF) verified parallel actions of all compounds, growth hormone may lodge more than one of the isolated growth factors mentioned above.

Another investigator treated a woman with Sheehan's syndrome in a dilated cardiomyopathy. Treatment in this case resulted in suppression of the dilated cardiomyopathy when the human growth hormone was continuously administered.

In all of the above-described cases the use of the hormone or the isolated growth factors brought beneficial results.

The inventor's published experimental investigations in rats and pigs have shown the ability to reconstruct the ventricular wall and to recognize other mechanisms linked to this treatment of myocardial ischemialacute necrosis.

SUMMARY OF THE INVENTION

It is an aspect of the invention to provide a method of treatment for acute myocardial infarction using human growth hormone.

It is an aspect of the invention to provide a method of treatment for acute myocardial infarction that provides a reduction of extension and intensity of the running necrosis limiting itself to a piece-meal type one, with partial intracellular lesions.

It is another aspect of the invention to a method of treatment for acute myocardial infarction that provides an absence of slippage and septal/ventricular ruptures.

Another aspect of the invention is to provide a method of treatment for acute myocardial infarction that reduces the incidence of ventricular aneurysms.

It is still another aspect of the invention to a method of treatment for acute myocardial infarction that restores the contractility in the previously affected, achynetic area.

It is another aspect of the invention to a method of treatment for acute myocardial infarction that improves the ventricular function.

It is another aspect of the invention to a method of treatment for acute myocardial infarction that lessens the incidence of ventricular arrythmias.

Finally, it is another aspect of the invention to a method of treatment for acute myocardial infarction that provides a beneficial treatment of cardiac failure.

The invention is a method of treating a patient to reduce heart damage associated with an acute myocardial infarction. The treatment comprises several first steps. First, a patient is selected based on a plurality of predetermined criteria to establish that the method of treatment is indicated. Then, the method of treatment is begun at a time ranging from immediately post onset to not more than ten hours post onset of the acute myocardial. Next, the patient is injected with an efficacious dose of human growth hormone for a predetermined period of time. Finally, the patient is tested on predetermined schedule to measure the effectiveness of the treatment. The damage to the patient's heart due to the acute myocardial infarction is substantially reduced than would be found if the patient had been untreated.

DETAILED DESCRIPTION OF THE INVENTION

A comparison was made among several myocardial patients who had exhibited a major or minor incidence of ventricular aneurysms. In spite of the fact that there were different etiologies present in those patients, a common pathophysiologic factor was sought and, also, the relation of that factor with inner elements of the cell, the myocardial collagen frame and the diverse pathological processes, which were acting in the different patients, were analyzed.

An investigation of comparative pathology was one of the first employed methods. This was completed with the study of the theoretical more important studies in the matter. Accordingly these parameters were analyzed: Chagas' Cardiomyophaty, which exhibits an incidence of more than 60% of ventricular aneurysms; a new pathologic model of diabetic cardiomyopathy, which was created by the inventor, experimentally, by means of a combination of human growth hormone and beta blockers. The incidence of ventricular aneurysms in this case was almost 70%. Ischemic cardiomyopathy (myocardial infarction) showed an incidence of ventricular aneurysms of 30%. Finally, there was an exotic entity, African Trypanosomiasis, it shows similar kind of lesions and the same distribution of them as in Chagas' disease but it also exhibits 2 particular sharp differences with respect to the other mentioned entities: the combined presence of granulatoma in the myocardial areas where lesions were extense and tend to break more than 2–3 layers of the myocardial depth in the left ventricule and the constant absence of ventricular aneurysms.

According to the above, an initial attention was focused on the scar tissue in the already mentioned myocardial entities. In this regard, all the evidence was pointing to the collagen framework without the exclusion of other possible factors involved. In several cases, the true role of the myocardial connective tissue was not particularly considered as in the cases of human myocardial infarction, despite an increasing knowledge of basic and experimentally investigations in this field.

Several observations of the inventor as well as the efforts of other investigators placed emphasis on certain accidents which were considered as clues to the running process to the formation of ventricular aneurysms. Among these clues are: the wavy fibers, followed by broken ones greater incidence in the left ventricule apex, etc. The correlation of those factors gave the possibility to gather all those elements, interrelating them dynamically with a theoretical geometrical model of formation of a ventricular aneurysm, disregarding the possibly different pathologies involved. An analysis of this theoretical model also provided several pharmacologic ideas in order to illuminate the feasibility of stopping the process leading to ventricular aneurysm during one of more of the critical steps of its formation, by means of reinforcement of the scar acting as a "barrier effect".

The geometric-dynamical model took into account several other factors like: module of the elasticity of the myocardial fibers, the particular spiral disposition of myocardial fibers in the myocardium, according to relatively recent works in this field. This helps to explain the major frequency of location of ventricular aneurysms at the apex. All the geometric and physical terms employed in the geometric-dynamical model have their counterparts in usual medical terms like: ventricular wall dilation; contagion= transmission of forces across the vicinity within a spiral disposition of the myocardial fibers; the barrier effect=scar; loss of elasticity of some fibers=wavy fibres. These fibers have lost elasticity, replacing it by plasticity, which is a variation of Hooke's law standards in normal fibres.

The second step of this investigation was an initial search of the myocardial collagen framework in several normal and pathologic conditions. Scanning electron microscopy and special stainings for the reticulum stroma in light microscopy were employed. The particular sequential aspect of the myocardial collagen framework during diverse stages of experimental infarctions was observed.

The third step was an effort to influence the collagen structure trying pharmacologically to achieve an actual reinforcement of its different fibers, particularly, in ischemic cardiomyopathy (AMI) in several animal models, mainly slippage, ventricular dilation, incidence of septal/free wall ruptures and ventricular aneurysms.

Several drugs were employed on this pourpose, human growth hormone was included among them with particular interest due to its stimulant action on fibroblasts.

Investigations were carried out in several series of animal models and everything was analyzed from different points of view. The published study took several years to complete.

Results achieved in acute experimental infarcts were repeatedly similar.

Summary of Findings in Human Growth Hormone Treated Cases:

1. A different outcome of the myocardial infarction, piece meal type of necrosis, compared to infarctions of control cases results. Planimetric differences between control and treated cases was significant.
2. Reduction of the incidence of ventricular aneurysms from 30% in control cases to 10% in treated-ones was a constant finding.
3. There was a virtual absence of ventricular dilation and slippage in all series. Slippage was always present in control cases; (it was particularly studied by means of Echo B in pigs.)
4. Ventricular contractility was restored in treated cases 48 and 72 hours post onset of infarction in the every area which appeared hypochynetic or achynetic at the beginning.
5. Preservation of all components of the myocardial collagen framework and a frank arrival of the new one were verified.
6. A lesser incidence of mortality in treated versus control animals was the rule.
7. Neoangiogenesis was a constant finding and could appropriately observed in infarcted pigs.

Differences between treated and control animals were found after diverse studies: Scanning and transmission Electron Microscopy. With them it was possible to observe the outstanding preservation of mitochondria.

An special study of the perimyocyte reticulum stroma was also performed. A definitive study with hydroxyproline was performed to measure the amount of scar tissue in control and treated cases. Van Gieson stain was used to see differences between them. Human growth hormone-treated animals exhibit a considerably lesser amount of necrotic tissue and concomitantly lower value of hydroxyproline.

Another study verified a marked reduction of corticoadrenal activity in treated-animals which is the opposite of the usual activity in non-treated acute myocardial infactions.

We may conclude that the different outcome of both groups of animals was verified through a complete experimental study and by all possible approaches.

Profound Mechanism of Action of Human Growth Hormone on Acute Myocardial

Infarcts

Up to the present time, treatment of coronary heart disease and myocardial infarction were centered in the concept of flow restorance to the affect arteries by means of pharmacologic or surgical procedures, whether simple or combined, sometimes in specific sequences.

Treatment of a myocardial infarction with human growth hormone paradoxically does not deal with mechanisms which try to restore the coronary flow, actually, it does not exert any influence on it. Basic actions of human growth hormone are to provide cellular protection. These actions of human growth hormone and isolated growth factors may be defined as the inhibition of a cell to trigger diverse mechanisms and to free certain compounds, after suffering an aggression, which may drive to a cellular necrosis.

The process may start when determined signals are elicited. Protecting compounds must be able to arrest that process. The situation appears similar to several mechanisms acting in cellular hibernation. In published hibernation studies, it was observed that the limitation in reaching very low temperatures was due to the possibility of ventricular fibrillation which always appears below 30° C. This limitation was overcome with the use of human growth hormone which raised the threshold for ventricular fibrillation.

The inventor has concluded that human growth hormone and isolated growth factors act as agents of cell protection in the cardiac cell; this protection stretches to metabolic preservation which also extends to the collagen framework of the myocardium.

Actions in the myocardium during an infarction do not end in what was described above, there are endocrine actions during the early period if necrosis by neutralizing and contraposing effects of adrenal compounds like cortisol and other cathecolamines. Antioxidant actions of the hormone are quite possible but were not studied yet.

During an ischemic insult to myocardial cells, once a typical necrotic process starts, it will be completed a little more than 24 hours afterwards when the molecular damnation was advanced and the structural jeopardy surpasses certain limits. Notwithstanding this fact, an efficacious treatment of infarctions must not be started after the first 7 to 8 hours due to the possible destruction of the mitochrondia and enzymes. The first reaction after an ischemic insult to myocardial cells will be the activation of certain growth factors in the macrophage: Tumor Necrosis Factor (TNF) and other interleukins: Platelet growth factor and Leukocyte growth factor. Actions of cortisol will persist during 4 days after the onset of infarction. At that time, inhibition of somatostatine will give raise to a free secretion of human growth hormone and the beginning of repair processes without inhibitions.

The opposite may be found in those treated-cases, the macrophage will switch its secretion to other growth factors, mainly Fibroblast growth factor (FGF); Insulin growth factor 1 (IGF1) and Transforming growth factor (TGF), etc. Actions of human growth hormone or those isolated growth factors will act in a dual way a) The cellular protection effect which is able to stop the evolution of the necrosis and b) anaplerotic actions of the hormone or of isolated growth factors, which include actions on the collagen framework of preservation and repair.

There are several differences between the inventor's treatment and the corresponding results obtained with human growth hormone and that of prior investigators. They found, in the dog model, some clues about repair processes during a myocardial infarction; the indiction of pulmonary neoangiogenesis and also within the myocardium. These findings were not backed by numerous experimental series of animals. The administered hormone, (Somatotropine) was originated by hypophyseal extraction with a limited availability, as it was common 30 years ago.

Bajusz in "Conditioning factors for cardiac necrosis", Intercontinental Medical Book Corporation, Verlag S. Karger-Basle, 1963, after the original investigations with Selye et al., "Arrested myocardial necrosis. An endocrine and multifactorial consequence of experimental treatment with human growth hormone", Abstracts 2 nd. International Symposium on Heart Failure. Mechanism and Management. Geneva, Switzerland, May 17, 1993, developed the concept of "cellular protection". The myocardium was not included in those experiences. As noted above, hibernation experiments with several compounds in order to increase the threshold of ventricular fibrillation revealed that Somatotropine was preferable, permitting the attainment of profound levels of artificial hibernation.

Our own investigations were performed with the special aim to positively influence several aspects which may occur during the evolution of an acute myocardial infarction. Those basic ideas were disclosed in "Ventricular Aneurysms: a Geometrical-Dynamical Model", Castagnino et al., Japan, J. Exp. Med. Vol. 59, 3, p. 89–102, 1989, incorporated herein by reference.

Summarizing, the objectives were:
a) To preserve at most the integrity of the collagen framework.
b) To avoid the secondary jeopardy related to lesions of the myocardial connective tissue: Myocardial/septal ruptures and dilation of the left ventricule. Reduction of the incidence of ventricular aneurysms after a collagen "barrier effect" was created by the aplerotic actions of human growth hormone. That was ascribed to a betterment of the myocardial scar.
c) An attempt to reach a "Myocardial protection" by the hormone through a mechanism which does not take into account the usual therapeutic methods employed in this entity, which point in general to surgical or pharmacologiv attempts to restore the critically arrested coronary flow.
d) To improve myocardial contractility and functional standards of the affected left ventricule.

The totality of objectives were reached and verified many times in several animal model and moumerous series with significant good results.

The same beneficial results were obtained in a recent pilot test performed with five human patients using the protocol that is the gist of this invention.

Possibly, the first documented case of beneficial action of human growth hormone in the myocardium was produced by Frustaci et al., "Reversible dilated cardiomyopathy due to growth hormone deficiency", Am. J. Clin. Pathol. 1992, 97(4): 503–508. Frustaci et al. found a dilated cardiomyopathy in a woman suffering a Sheeban's Syndrome and human growth hormone was administered as a replacing therapy. A normalized ventricular size was found after a short time of continuous hormonal treatment.

However, Frustaci's method of treatment using human growth hormone was not recognized as being potentially useful for the treatment of human acute myocardial infarctions.

Other authors made investigations on diverse animal models with isolated growth factors which exhibit similar actions, on the myocardium as the human growth hormone. The objective of those studies was different that the inventor's goals that they only made a particular search of a circulation betterment of the coronary capillary vessels.

In contrast, the inventor developed a method treatment to use human growth hormone for acute myocardial infarctions.

Adverse, definitive known adverse effects due to the administration of this compound during a prolonged period were not considered since this treatment relates to an acute situation. The long term adverse effects of the compound have been investigated by others who administered human growth hormone to overcome several deficiencies of old age. Patients received human growth hormone in high doses during several months.

For the purposes of investigating the suitability of human growth hormone treatment for AMI, the following patient types were considered as not being eligible for the first tests. This does not necessarily imply that such patients may not later be included in the pool where this type of treatment is indicated. The list of patients excluded is as follows:

1. Patients recently taking beta blockers (within 15 to 20 days of the test date).
2. Patients taking adrenal corticosteroids.
3. Patients also taking non-corticosteroid anti-inflammatory drugs.
4. Patients with known-active-diagnosed tumors.
5. Diabetic coma, until its compensation with Insulin.

Hypertension was not considered as a parameter that would exclude a patient from participating or one that might require an abrupt termination if such a hypertensive situation should develop during the course of treatment.

There was no age limitation set for eligibility. Due to Helinski protocols and ethical reasons, the inventor did not administer human growth hormone in acute myocardial infarctions as a first choice. Rather, this treatment was used for those patients that exhibited a failure to a classic first choice treatment with thrombolytics procedures and other or arrived later than the recommended periods to employ the classic methods.

Clinical diagnosis of acute myocardial infarction was made by three methods well known in the art . . . clinical, electrocardiography, enzymes.

The preferable time for the administration of human growth hormone was determined to be substantially less than ten hours from the time of the onset of the infarction. This was due to course of damage, particularly damage to respiratory enzymes and mitochondria, which may become irreversible after that time. Selected topography of infarction was limited to the anterior ventricular wall.

The preferred method is to subcutaneously inject human growth hormone into the patient twice daily for a period of seven days. The preferred dose is two (2) International Units per kilogram of body weight per week. Consequently, the daily dose was approximately 20 IU or a total of 140 IU. NORDITROPIN as manufactured by Novo-Nordisk Pharmaceutical, Inc. of Princeton, New Jersey, is the preferred version of human growth hormone.

According to the initial limitation of the pilot trial test, the follow up and particular studies of every patient were limited to:

a) Routine: clinics, electrocardiography, enzymes and usual blood test: cells and chemistry.

b) Echo B: It was considered as one of the most important and objective tool for evaluation:
  1) To measure dimensions of ventricular wall;
  2) Scores of contractility
  3) Whether contractility was restored
  4) Presence or absence of dilation of ventricular cavities.

c) Gama camera: (Technetium). Comparison of results to those Echo concerning dimensions of ventricular walls and cavities. Difference of perfused areas.

Preliminary results in human cases were as follows:

1) Absence of ventricular wall thinning by slippage. No dilation of cavities.

2) Absence of early ruptures, whether of septal or of free ventricular origin.

3) Initial achynetic-hypochynetic area (location of the infarcted ventricular wall). The septum or both turns after 48–72 hours into normal contracting areas.

4) Increased contractility in the rest of the wall of left ventricule is an usual finding.

5) Absence of ventricular arrythmias.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. A method of treating a patient to reduce heart damage associated with an acute myocardial infarction comprising the steps of:

selecting a patient having had an acute myocardial infarction to establish that the method of treatment is indicated;

beginning the method of treatment at a time ranging from immediately post onset to not more than ten hours post onset of the acute myocardial infarction;

injecting the patient with an efficacious dose of human growth hormone;

testing the patient to measure the effectiveness of the treatment;

wherein the damage to the patient's heart due to the acute myocardial infarction is substantially reduced compared to the damage to the patient's heart if the patient had been untreated with said method.

2. The method of claim 1 wherein the efficacious dose used in the injecting step is measured as two international units per kilogram of the patient's body weight per week of treatment.

3. The method of claim 2 wherein a predetermined length of time for the method of treatment is two injections per day for seven days.

4. The method of claim 3 wherein the injecting step is performed subcutaneously.

5. The method of claim 4 wherein the testing step further comprises the steps of:

performing routine clinical, electrocardiography, enzyme and blood tests on the patient;

evaluating the patient's heart using Echo B techniques;

analyzing the ventricular walls and cavities using a gamma camera.

* * * * *